United States Patent

Kato et al.

[11] Patent Number: 4,652,574
[45] Date of Patent: Mar. 24, 1987

[54] CERTAIN MONO-, DI- OR TRI-SUBSTITUTED PYRIDYL ESTERS OF ALKANE SULFONIC ACIDS HAVING INSECTICIDAL, ACARICIDAL AND NEMATOCIDAL PROPERTIES

[75] Inventors: Shoichi Kato; Shizuo Shimano; Tatsumi Hayaoka, all of Ageo; Akio Masui, Omiya, all of Japan

[73] Assignee: Nippon Kayaku Kabushiki Kaisha, Tokyo, Japan

[21] Appl. No.: 796,922

[22] Filed: Nov. 12, 1985

[30] Foreign Application Priority Data

Nov. 14, 1984 [JP] Japan .................................. 59-240150
May 21, 1985 [JP] Japan .................................. 60-106995

[51] Int. Cl.⁴ ..................... A01N 43/40; C07D 213/71
[52] U.S. Cl. ..................................... 514/347; 546/294; 546/295
[58] Field of Search ................. 546/294, 295; 514/347

[56] References Cited

FOREIGN PATENT DOCUMENTS 1242057 8/1971 United Kingdom ................ 546/295

Primary Examiner—Alan L. Rotman
Attorney, Agent, or Firm—John P. White

[57] ABSTRACT

A compound of the formula:

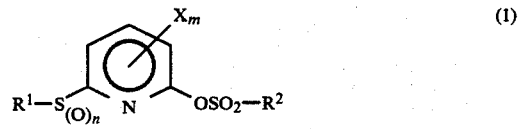

wherein $R^1$ is $C_1$–$C_{12}$alkyl, $R^2$ is $C_1$–$C_{12}$alkyl or $C_1$–$C_4$alkyl which is substituted with halogen, X is halogen, m is 0, 1 or 2 and n is 0, 1 or 2, a process for producing said compound and use thereof as an insecticide acaricide and nematicide.

6 Claims, No Drawings

CERTAIN MONO-, DI- OR TRI-SUBSTITUTED PYRIDYL ESTERS OF ALKANE SULFONIC ACIDS HAVING INSECTICIDAL, ACARICIDAL AND NEMATOCIDAL PROPERTIES

DETAILED DESCRIPTION OF THE INVENTION

The present invention relates to an alkanesulfonate derivative represented by the general formula:

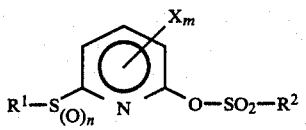
(1)

wherein $R^1$ is $C_1$–$C_{12}$ alkyl, $R^2$ is $C_1$–$C_{12}$ alkyl or $C_1$–$C_4$ alkyl which is substituted with halogen, X is halogen, m is 0, 1 or 2 and n is 0, 1 or 2,
a process for preparing it and an insecticidal or acaricidal, nematicide composition containing it. A compound represented by the general formula (1) can be used as an insecticide, acaricide or nematicide in paddy fields, plowed fields, fruit farms, forests or the like.

Certain alkanesulfonate derivatives are known to be useful as an active ingredient of an insecticide or a nematicide.

For example, 3-n-butylthiophenyl methanesulfonate and 3-ethylsulfonylphenyl methanesulfonate are described to be useful as an insecticide in Japanese Patent Publication No. 3898/1968 and Japanese Patent Laid-Open No. 98025/1973, respectively. Further, it is reported in J. Agr. Food Chem. 18(1), 57 (1970) that 6-chloro-2-pyridyl methanesulfonate has a nematicidal effect.

Alkanesulfonate derivatives of the prior art have an insufficient insecticidal effect on insect pests which have acquired a resistance to organic phosphate or carbamate insecticides or the like, and insect pests exhibiting a high susceptibility, so that a compound which can prevent such insect pests with a small amount has been desired.

The inventors of the present invention have found that a compound having a high insecticidal, acaricidal or nematicidal effect can be obtained by substituting the pyridine ring with an alkylthio, alkylsulfinyl or alkylsulfonyl group at the 6-position and with an alkanesulfonyloxy group at the 2-position as shown by the general formula:

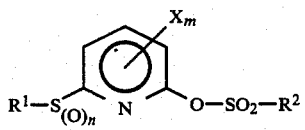
(1)

wherein $R^1$ is $C_1$–$C_{12}$ alkyl, $R^2$ is $C_1$–$C_{12}$ alkyl or $C_1$–$C_4$ alkyl which is substituted with halogen, X is halogen, m is 0, 1 or 2 and n is 0, 1 or 2.

A compound represented by the general formula (1) can be prepared by reacting a compound represented by the general formula:

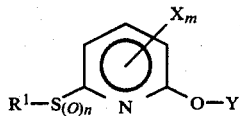
(2)

wherein $R^1$, X, m and n are as defined above and Y is a hydrogen, alkali or alkaline earth metal atom,
with a sulfonyl chloride represented by the general formula:

(3)

wherein $R^2$ is as defined above,
or a sulfonic acid anhydride represented by the general formula:

(4)

wherein $R^2$ is as defined above,
in a solvent, if necessary, in the presence of an acid binding agent, at a temperature of $-10°$ to $100°$ C., preferably $0°$ to $40°$ C., for 0.5 to 10 hours.

Examples of the solvent to be used include water, aromatic hydrocarbons such as benzene, toluene and xylene; aliphatic hydrocarbons such as hexane, heptane and petroleum benzine; halogenated hydrocarbons such as chloroform and dichloromethane; aprotic polar solvents such as dimethylformamide and dimethyl sulfoxide; lower alcohols such as methanol and ethanol; ethers such as diisopropyl ether; diethyl ether, 1,2-dimethoxyethane, tetrahydrofuran and dioxane; nitriles such as acetonitrile and propionitrile; ketones such as acetone, diisopropyl ketone and methyl ethyl ketone. Examples of the acid binding agent include alkali metal hydroxides such as NaOH and KOH; alkaline earth metal hydroxides such as $Ca(OH)_2$ and $Mg(OH)_2$; alkali metal hydrides such as sodium hydride; alkali metal alcoholates such as sodium alcoholate; alkali metal oxides such as $Na_2O$ and $K_2O$; alkali metal carbonates such as soda ash; sodium amide; aliphatic and aromatic tertiary amines such as triethylamine, dialkylaniline and pyridine.

In addition, silver oxide can be used as an acid binding agent.

Additionally, a phase transfer catalyst, for example, tetra-n-butylammonium bromide or triethylbenzylammonium chloride, may also be used to obtain the objective alkanesulfonate derivative in a high yield.

A compound represented by the general formula (1) wherein n is 1 or 2 can be prepared by obtaining a compound represented by the general formula (5)

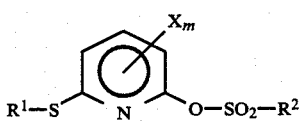
(5)

which corresponds to the compound represented by the general formula (1) wherein n is 0 and then treating the obtained compound with an oxidizing agent such as hydrogen peroxide. That is, when the obtained compound represented by the general formula (5) is treated in acetic acid containing 1.0 to 3.0 times by mol as much hydrogen peroxide as the compound represented by the general formula (5) at $0°$ to $50°$ C. for 3 to 7 hours, a compound represented by the general formula (1) wherein n is 1 can be obtained, while when the compound of the general formula (1) wherein n is 0 or 1 are treated in acetic acid containing 2.0 to 5.0 times by mol as much hydrogen peroxide at 0° to 100° C., preferably at 60° to 100° C., for 2 to 5 hours, a compound represented by the general formula (1) wherein n is 2 can be obtained in a high yield. In this treatment, alcohols such as t-butanol, acetone, water and their mixture can be used as a solvent in place of acetic acid.

Examples of the oxidizing agent to be used in oxidizing a compound represented by the general formula (1) wherein n is 0 into the corresponding compound of the general formula (1) wherein n is 1 include organic peroxides, halides, periodates, nitrogen oxides, ozone, metal oxides, and singlet oxygen as well as hydrogen peroxide. Additionally, this oxidation can be carried out by air or anodic oxidation.

Examples of the oxidizing agent to be used in oxidizing a compound represented by the general formula wherein n is 0 or 1 into the corresponding compound represented by the general formula (1) wherein n is 2 include peroxy acids, hydroperoxides, halogen, halogenating agents, ozone, oxygen/transition metal catalyst, potassium peroxysulfate, potassium permanganate, dinitrogen tetraoxide, sodium metaperiodate, osmium oxide (VIII), ruthenium oxide (VIII), sodium dichromate, and nitric acid as well as hydrogen peroxide. Additionally, the oxidation with electrodes is possible.

The pyridinol derivative represented by the general formula (2) which is a starting material can be prepared by the known methods (see, for example, U.S. Pat. No. 3,335,146), that is, by reacting 6-halogenpyridinol with an alkyl mercaptan.

Examples of the $C_1$–$C_{12}$ alkyl which is $R^1$ or $R^2$ in the general formula (1) include methyl, ethyl, n-propyl, iso-propyl, n-butyl, sec-butyl, iso-butyl, n-amyl, iso-amyl, sec-amyl, n-hexyl, n-octyl and n-lauryl. Examples of the $C_1$–$C_4$ alkyl substituted with halogen include chloromethyl, trifluoromethyl 2-chloroethyl, 3-chloropropyl, 3-bromopropyl and 4-chlorobutyl.

The compounds of the present invention may be used alone if desired, but they are generally formulated by blending suitable adjuvants to improve or stabilize the effects thereof and used as such or after being diluted if necessary. The compounds of the invention can be formulated in the conventional manners well-known in the art in any convenient form such as dust, granule, micro granule, wettable powder, flowable, emulsion, microcapsule, oil, aerosol, heating fumigant (e.g. mosquito repellent of an incense type or electric type), fuming agent such as fogging, non-heating fumigant, or toxic feed.

Examples of said adjuvants are carrier (i.e. diluent) and other adjuvants such as a spreader, emulsifying agent, wetting agent, dispersing agent, fixing agent or disintegrator. Examples of the liquid carrier are aromatic hydrocarbons such as toluene or xylene; alcohols such as methanol, butanol or glycol; ketones such as acetone; amides such as dimethylformamide; sulfoxides such as dimethyl sulfoxide; methylnaphthalene; cyclohexane, animal or vegetable oils; fatty acids; fatty acid esters or the like as well as petroleum distillates such as kerosine or gas oil.

Examples of the solid carrier are clay, kaolin, talc, diatomaceous earth, silica, calcium carbonate, montmorillonite, bentonite, feldspar, quartz or saw dust.

Surfactants are generally used as an emulsifying or dispersing agent. Examples of them are anionic, cationic, non-ionic and ampholytic surfactants such as sodium salt of higher alcohol sulfate, stearyltrimethylammonium chloride, polyoxyethylene alkylphenyl ether or laurylbetaine.

Examples of the spreaders are polyoxyethylene nonylphenyl ether and polyoxyethylene lauryl ether. Examples of the wetting agent are polyoxyethylene nonylphenyl ether and dialkyl sulfosuccinate. Examples of the fixing agent are carboxymethylcellulose and polyvinyl alcohol. Examples of the disintegrator are sodium ligninsufonate and sodium lauryl sulfate.

Furthermore, it is possible to blend two or more compounds of the present invention to obtain an improved insecticidal or acaricidal activity. In addition, it is also possible to use a compound of the present invention simultaneously with other physiologically active substances such as pyrethroids, e.g., allethrin, phthalthrin, permethrin, decamethrin, fenvalerate, or α-cyano-3-phenoxybenzyl, 2,2-dichloro-1-(4-ethoxyphenyl)-cyclopropane-1-carboxylate, and various isomers thereof, pyrethrum extract, organosphosphorus pesticides, e.g., DDVP, fenitrothion, diazinon or temefos, carbamate pesticides, e.g., NAC, MTMC, BPMC or pirimor, other pesticides, acaricides, bactericides, nematicides, herbicides, plant growth regulators, fertilizers, BT, insect hormones or other pesticides, thereby affording a multipurpose composition which exhibits an improved effect and further a synergistic effect, if things go well.

It is further possible to increase the effect of the composition several-fold by adding synergists for pyrethroids such as piperonyl butoxide, sulfoxide or safroxane.

Although the compounds of the present invention are stable to light, heat, oxidation or the like, antioxidant or ultraviolet absorber such as phenols, e.g., BHT or BHA, arylamines, e.g., α-naphthylamine, or benzophenone compounds may be added as a stabilizer to prepare a composition which exhibits a higher stability, if desired.

The content of active ingredients in the composition of the present invention varies depending on the conditions of use such as formulation form or application method, and is usually from 0.2 to 95% by weight, preferably from 0.5 to 80% by weight, although the active ingredient may be used alone in a special case.

The composition of the present invention may be used in an amount which depends on the conditions such as formulation form, season or method for application. Generally, it is used in an amount of 10 to 300 g/10 a (a=100 m$^2$), and preferably 15 to 200 g/100 a (in terms of the active ingredient) for the control of insect pests in ornamental forest or livestock and in an amount of 2 to 200 mg/m$^2$, preferably 5 to 100 mg/m$^2$ (in terms of the active ingredient) for the purpose of exterminating hygienic insect pests. For example, from 15 to 120 g/10 a of the active ingredient is used in the case of dust, 30 to 240 g/10 a thereof is used in the case of granule and 40 to 250 g/10 a thereof is used in the case of emulsion or wettable powder. However, it may be possible, or even necessary, to use the active ingredient in an amount which is outside the range as specified above, in a special case.

The insect pests on which the pesticides, acaricides and nematicides of the present invention are effective are as follows; HEMIPTERA such as *Nephotettix cincticeps, Sogatella furcifera, Nilaparvata lugens, Laodel-* phax striatellus, Riptortus clavatus, Nezara viridula, Stephanitis nashi, Trialeurodes vaporariorum, Aphis gossypii, Myzus persicae and Unaspis yanonensis; LEPIDOPTERA such as Phyllonorycter ringoneella, Plutella xylostella, Promalactis inonisema, Adoxophyes orana, Leguminivora glycinivorella, Cnaphalocrocis medinalis, Chilo suppressalis, Ostrinia furnacalis, Mamestra brassicae, Pseudaletia separata, Spodoptera litura, Parnara guttata and Pieris rapae crucivora; COLEOPTERA such as Anomala cuprea, Popillia japonica, Echinocnemus soqameus, Lissorhoptrus oryzophilus, Oulema oryzae, Anthrenus verbasci, Tenebroides mauritanicus, Sitophilus zeamais, Henosepilachna vigintioctopunctata, Callosobruchus chinensis, Monochamus alternatus and Aulacophora femoralis; HYMENOPTERA such as Athalia rosae japonensis and Arge similis; DIPTERA such as Culex pipiens fatigans, Aedes aegypti, Asphondylia sp., Hylemya platura, Musca domestica vicinia, Dacus cucurbitae and Agromyza oryzae; APHANIPTERA such as Pulex irritans, Xenopsylla cheopis and Ctenocephalides canis; THYSANOPTERA such as Scirtothrips dorsalis, Thrips tabaci, Thrips palmi and Baliothrips biformis; ANOPLURA such as Pediculus humanus corporis and Phthirus pubis; PSOCOPTERA such as Trogium pulsatorium and Liposcelis bostrychophus; ORTHOPTERA such as Gryllotalpa africana, Locusta migratoria, Oxya yezoensis, Blattella germanica and Periplaneta fuliginosa and ACARINA such as Tetranychus urticae, Panonychus citri, Tetranychus cinnabarinus, Tetranychus kanzawai and Rhizoglyphus echinopus.

The nematodes on which the nematicides of the present invention are effective are TYLENCHIDA such as Heterodera glycines, Heterodera elachist, Meloidogyne incognita, Pratylenchus neglectus, Aphelenchoides besseyi, Aphelenchoides ritzemabosi and Bursa phelenchus lignicolus.

The compound of the present invention is an excellent insecticide, acaricide or nematicide and can prevent insect pests effectively by contacting them with the compound. Alternatively, it can prevent insect pests on leaves by applying it at the root of plants. The compound has characteristics as a systemic insecticide without any phytotoxicity on the host crops.

Now, the present invention will be described by Examples.

SYNTHESIS EXAMPLE

Synthesis Example 1

6-n-Propylthio-2-pyridyl methanesulfonate (No. 1)

3.4 g of 6-n-propylthio-2-pyridinol and 2.2 g of anhydrous sodium carbonate were suspended in 25 ml of N,N-dimethylformamide, followed by stirring. 2.4 g of methanesulfonyl chloride was added dropwise to the suspension at 10° C. After the addition, the bath was removed and the resulting mixture was allowed to stand to raise the temperature of the mixture to room temperature. The mixture was heated to 50° C. and stirred for 2.5 hours. The reaction mixture was poured into 200 ml of chilled water and extracted with ether twice. The ether layer was washed with 5% aqueous caustic soda solution and water and dried over anhydrous sodium sulfate. The residue obtained by distilling away the solvent was purified by silica gel column chromatography (with toluene and n-hexane) to obtain 3.9 g of 6-n-propylthio-2-pyridyl methanesulfonate as a pale yellow oil (yield: 78.8%).

$n_D^{25}$ 1.5465

PMR(CCl$_4$), δ: 1.00 (t, 3H), 1.78 (q, 2H), 3.07 (t, 2H), 3.34 (s, 3H), 6.73 (d, 1H), 7.09 (d, 1H), 7.58 (d, 1H) ppm.

Synthesis Example 2

Synthesis of 6-isopropylsulfonyl-2-pyridyl methanesulfonate (No. 22)

2.2 g of 6-isopropylsulfonyl-2-pyridinol and 1.48 g of methanesulfonyl chloride were dissolved in 30 ml of methylene chloride. 1.65 g of triethylamine was added dropwise to the solution at 10° C. or below. The mixture was stirred at room temperature for 2 hours and at 50° to 60° C. for 2 hours to complete the reaction. The reaction mixture was poured into 100 ml of chilled water to separate the methylene chloride layer. The water layer was further extracted with methylene chloride. The resulting organic layer was combined with the above methylene chloride layer. The combined layer was washed with water and chilled to remove the solvent. The resulting residue was purified by silica gel column chromatography (with ethyl acetate and n-hexane) to obtain 2.4 g of objective 6-isopropylsulfonyl-2-pyridyl methanesulfonate as a colorless crystal (yield: 76.0%).

m.p. 70.5°–71.5° C.

PMR(CCl$_4$), δ: 1.40 (d, 3H), 3.69 (s, 3H), 3.51–3.88 (m, 1H), 7.57–7.74 (m, 1H), 8.30–8.57 (m, 2H) ppm.

Synthesis Example 3

Synthesis of 6-isobutylthio-2-pyridyl trifluoromethanesulfonate (No. 39)

A mixture of 6.5 g of 6-isobutylthio-2-pyridinol and 50 ml of pyridine was stirred and cooled to 10° C. or below. 10 g of trifluoromethanesulfonic anhydride was added dropwise to the mixture. The temperature of the resulting mixture was brought to room temperature and the mixture was stirred at this temperature for 2 hours and at 50° to 60° C. for one hour to complete the reaction. The reaction mixture was poured into 200 ml of chilled water and extracted with benzene twice. The residue obtained by distillating away the benzene was purified by silica gel column chromatography (with toluene and n-hexane) to obtain 9.3 g of objective 6-isobutylthio-2-pyridyl trifluoromethanesulfonate as a colorless oil (yield: 84.3%).

$n_D^{25}$ 1.4827

PMR(CDCl$_3$) δ: 1.04 (d, 6H), 1.98 (m, 1H), 3.04 (d, 2H), 6.76 (d, 1H), 7.20 (d, 1H), 7.59 (t, 1H) ppm.

Synthesis Example 4

Synthesis of 6-n-propylsulfinyl-2-pyridyl methanesulfonate (No. 2)

2.83 g of 6-n-propylthio-2-pyridyl methanesulfonate (No. 1) was dissolved in 20 ml of acetic acid. 1.7 ml of 35% aqueous hydrogen peroxide was added dropwise to the obtained solution at room temperature. The resulting mixture was stirred for 3.5 hours. 1 ml of 35% aqueous hydrogen peroxide was added to the mixture and the reaction was continued for 3 hours. The reaction mixture was poured into 50 ml of chilled water and extracted with toluene twice. The toluene layer was washed with 5% NaOH until it was neutralized, washed with water, dried over anhydrous sodium sulfate and distilled to remove the solvent, thus obtaining 2.2 g of 6-n-propylthiosulfinyl-2-pyridyl methanesulfonate as a colorless crystal (yield: 73.3%).

m.p. 51°–53° C.

PMR(CDCl₃) δ: 1.06 (t, 3H), 1.75 (m, 2H), 2.94 (m, 2H), 3.47 (s, 3H), 7.19 (t, 1H), 7.88–8.15 (m, 2H) ppm.

Synthesis Example 5

Synthesis of 6-n-propylsulfonyl-2-pyridyl methanesulfonate (No. 3)

2.2 g of 6-n-propylthio-2-pyridyl methanesulfonate (No. 1) was dissolved in 30 ml of acetic acid. 2.6 ml of 35% aqueous hydrogen peroxide was added to the solution at room temperature. The obtained mixture was stirred at 80° to 90° C. for 40 hours to complete the reaction. The reaction mixture was poured into water and extracted with methylene chloride twice. The extract was washed with 5% aqueous caustic soda until it was neutralized, washed with water, dried over anhydrous sodium sulfate and distilled to remove the solvent, thus obtaining 1.6 g of 6-n-propylsulfonyl-2-pyridyl methanesuolfonate as a light brown oil (yield: 68.3%).

$n_D^{25}$ 1.5287

PMR(CDCl₃) δ: 1.03 (t, 3H), 1.77 (m, 2H), 3.33 (m, 2H), 3.58 (s, 3H), 7.46 (d, 1H), 8.06–8.34 (m, 2H) ppm.

Other compounds of the present invention were synthesized according to the same procedures as the ones described in Synthesis Examples 1 to 5.

Representative compounds among the obtained ones are shown in Table 1.

TABLE 1

$$R^1-S_{(O)_n}\text{-pyridyl-}O-SO_2-R^2$$

| No. | R¹ | n | R² | Yield (%) | $n_D^{25}$ (mp) | Appearance |
|---|---|---|---|---|---|---|
| 1 | CH₃CH₂CH₂— | 0 | CH₃ | 78.8 | 1.5465 | pale yellow oil |
| 2 | CH₃CH₂CH₂— | 1 | CH₃ | 73.3 | (51~53° C.) | colorless crystal |
| 3 | CH₃CH₂CH₂— | 2 | CH₃ | 68.3 | 1.5287 | Light brown oil |
| 4 | CH₃CH₂CH₂— | 0 | —CH₂CH₃ | 90.1 | 1.5410 | pale yellow oil |
| 5 | CH₃CH₂CH₂— | 1 | —CH₂CH₃ | 87.9 | 1.5322 | colorless oil |
| 6 | CH₃CH₂CH₂— | 2 | —CH₂CH₃ | 89.1 | 1.5159 | colorless oil |
| 7 | (CH₃)₂CHCH₂— | 0 | CH₃ | 70.2 | (40~40.5° C.) | colorless crystal |
| 8 | (CH₃)₂CHCH₂— | 1 | CH₃ | 91.9 | (87.5~88.5° C.) | colorless crystal |
| 9 | (CH₃)₂CHCH₂— | 2 | CH₃ | 89.1 | 1.5156 | colorless oil |
| 10 | (CH₃)₂CHCH₂— | 0 | —CH₂CH₃ | 78.5 | 1.5332 | colorless oil |
| 11 | (CH₃)₂CHCH₂— | 1 | —CH₂CH₃ | 83.4 | 1.5256 | " |
| 12 | (CH₃)₂CHCH₂— | 2 | —CH₂CH₃ | 84.6 | (48.5~49.5° C.) | colorless crystal |
| 13 | CH₃CH₂CH₂— | 0 | —CH₂CH₂CH₃ | 65.9 | 1.5349 | colorless oil |
| 14 | CH₃CH₂— | 0 | CH₃ | 66.5 | 1.5546 | colorless oil |
| 15 | CH₃CH₂— | 0 | —CH₂CH₃ | 97.0 | 1.5476 | " |
| 16 | CH₃CH₂CH₂— | 0 | —CH(CH₃)₂ | 33.6 | 1.5345 | " |
| 17 | CH₃CH₂CH₂— | 0 | —CH₂CH₂CH₂CH₃ | 86.4 | 1.5290 | colorless oil |
| 18 | CH₃CH₂CH₂— | 2 | —CH₂CH₂CH₂CH₃ | 90.0 | 1.5090 | " |

TABLE 1-continued $$R^1-S(O)_n- \text{(pyridine)} -O-SO_2-R^2$$

| No. | R¹ | n | R² | Yield (%) | $n_D^{25}$ (mp) | Appearance |
|---|---|---|---|---|---|---|
| 19 | (CH₃)₂CH— | 0 | CH₃ | 92.2 | 1.5444 | " |
| 20 | (CH₃)₂CH— | 1 | CH₃ | 87.4 | 1.5412 | " |
| 21 | (CH₃)₂CH— | 2 | CH₃ | 76.0 | (70.5~71.5° C.) | colorless crystal |
| 22 | CH₃CH₂CH(CH₃)— | 0 | CH₃ | 86.6 | 1.5420 | colorless oil |
| 23 | CH₃CH₂CH(CH₃)— | 1 | CH₃ | 87.0 | 1.5302 | " |
| 24 | CH₃CH₂CH(CH₃)— | 2 | CH₃ | 89.1 | 1.5210 | " |
| 25 | CH₃CH₂CH₂CH₂— | 0 | CH₃ | 90.1 | 1.5320 | brown oil |
| 26 | CH₃CH₂CH₂CH₂— | 1 | CH₃ | 72.2 | 1.5321 | pale yellow oil |
| 27 | CH₃CH₂CH₂CH₂— | 2 | CH₃ | 78.5 | 1.5142 | " |
| 28 | CH₃CH₂CH₂CH₂CH₂— | 0 | CH₃ | 74.5 | 1.5362 | " |
| 29 | CH₃CH₂CH₂CH₂CH₂— | 2 | CH₃ | 94.6 | (65~67° C.) | colorless crystal |
| 30 | (CH₃)₂CHCH₂CH₂— | 0 | CH₃ | 74.5 | 1.5356 | pale yellow oil |
| 31 | (CH₃)₂CHCH₂CH₂— | 1 | CH₃ | 90.1 | 1.5281 | colorless oil |
| 32 | (CH₃)₂CHCH₂CH₂— | 2 | CH₃ | 85.1 | 1.5145 | colorless oil |
| 33 | (CH₃CH₂)₂CH— | 0 | CH₃ | 52.2 | 1.5371 | pale yellow oil |
| 34 | (CH₃CH₂)₂CH— | 2 | CH₃ | 88.5 | 1.5160 | colorless oil |
| 35 | CH₃— | 0 | CH₃ | 68.4 | 1.5633 | " |
| 36 | CH₃— | 2 | CH₃ | 56.2 | (64~65° C.) | colorless crystal |
| 37 | (CH₃)₂CHCH₂— | 0 | —CH₂Cl | 58.4 | 1.5430 | pale yellow oil |

TABLE 1-continued $$R^1-S(O)_n \underset{N}{\bigcirc} O-SO_2-R^2$$

| No. | R¹ | n | R² | Yield (%) | $n_D^{25}$ (mp) | Appearance |
|---|---|---|---|---|---|---|
| 38 | (CH₃)₂CHCH₂— | 2 | —CH₂Cl | 86.6 | 1.5240 | colorless oil |
| 39 | (CH₃)₂CHCH₂— | 0 | CF₃ | 84.3 | 1.4827 | " |
| 40 | (CH₃)₂CHCH₂— | 1 | CF₃ | 96.3 | 1.4789 | " |
| 41 | (CH₃)₂CHCH₂— | 2 | CF₃ | 95.2 | 1.4707 | " |
| 42 | (CH₃)₂CHCH₂— | 0 | —CH₂CH₂CH₃ | 75.9 | 1.5291 | " |
| 43 | (CH₃)₂CHCH₂— | 2 | —CH₂CH₂CH₃ | 85.2 | 1.5086 | " |
| 44 | n-C₁₂H₂₅— | 0 | CH₃ | 81.6 | (46~46.5° C.) | colorless crystal |
| 45 | n-C₁₂H₂₅— | 1 | CH₃ | 91.4 | (63~64° C.) | colorless crystal |
| 46 | n-C₁₂H₂₅— | 2 | CH₃ | 91.4 | (73.5~74° C.) | " |
| 47 | n-C₈H₁₇— | 0 | CH₃ | 74.2 | 1.5228 | light brown oil |
| 48 | n-C₈H₁₇— | 1 | CH₃ | 87.6 | (49~50.5° C.) | colorless crystal |
| 49 | n-C₈H₁₇— | 2 | CH₃ | 81.8 | (58~59.5° C.) | " |
| 50 | CH₃CH₂CH₂— | 2 | —CH₂CH₂CH₃ | 86.1 | 1.5119 | colorless oil |
| 51 | CH₃CH₂CH₂— | 2 | —CH(CH₃)₂ | 89.6 | 1.5143 | " |
| 52 | (CH₃)₂CHCH₂— | 0 | —CH₂CH₂CH₂Cl | 95.2 | 1.5412 | " |
| 53 | (CH₃)₂CHCH₂— | 1 | —CH₂CH₂CH₂Cl | 80.7 | (44~46° C.) | colorless crystal |
| 54 | (CH₃)₂CHCH₂— | 2 | —CH₂CH₂CH₂Cl | 81.6 | (66~67° C.) | " |
| 55 | (CH₃)₂CHCH₂— | 0 | —CH(CH₃)₂ | 47.0 | 1.5291 | pale yellow oil |

TABLE 1-continued $$R^1-S(O)_n-\underset{N}{\text{pyridine}}-O-SO_2-R^2$$

| No. | R¹ | n | R² | Yield (%) | $n_D^{25}$ (mp) | Appearance |
|---|---|---|---|---|---|---|
| 56 | (CH₃)₂CHCH₂— | 1 | —CH(CH₃)₂ | 77.1 | 1.5201 | " |
| 57 | (CH₃)₂CHCH₂— | 2 | —CH(CH₃)₂ | 90.2 | 1.5079 | colorless oil |
| 58 | (CH₃)₂CHCH₂— | 0 | —C₅H₁₁(n) | 48.1 | 1.5228 | light brown oil |
| 59 | (CH₃)₂CHCH₂— | 1 | —C₅H₁₁(n) | 86.2 | 1.5147 | colorless oil |
| 60 | (CH₃)₂CHCH₂— | 2 | —C₅H₁₁(n) | 84.8 | 1.5046 | " |
| 61 | (CH₃)₂CHCH₂— | 0 | —C₈H₁₇(n) | 44.2 | 1.5128 | pale yellow oil |
| 62 | (CH₃)₂CHCH₂— | 1 | —C₈H₁₇(n) | 79.8 | 1.5077 | colorless oil |
| 63 | (CH₃)₂CHCH₂— | 2 | —C₈H₁₇(n) | 91.8 | 1.4971 | " |
| 64 | CH₃CH₂CH(CH₃)— | 0 | —C₂H₅ | 83.8 | 1.5358 | pale yellow oil |
| 65 | CH₃CH₂CH(CH₃)— | 1 | —C₂H₅ | 94.5 | 1.5282 | colorless oil |
| 66 | CH₃CH₂CH(CH₃)— | 2 | —C₂H₅ | 89.6 | 1.5160 | pale yellow oil |
| 67 | CH₃CH(CH₃)— | 0 | —C₂H₅ | 80.8 | 1.5390 | pale yellow oil |
| 68 | CH₃CH(CH₃)— | 1 | —C₂H₅ | 82.5 | 1.5308 | colorless oil |
| 69 | CH₃CH(CH₃)— | 2 | —C₂H₅ | 89.1 | 1.5189 | pale yellow oil |

Synthesis Example 6

3-Chloro-6-ethylthio-2-pyridyl methanesulfonate (No. 70)

5 g of 3-chloro-6-ethylthio-2-pyridinol and 3.7 g of methanesulfonyl chloride were dissolved in 50 ml of methylene chloride, followed by stirring. 4 g of triethylamine was added dropwise to the solution at 10° C. or below and the obtained mixture was allowed to stand to lower the temperature to room temperature. The mixture was heated to 40° C. and stirred for 2 hours. 50 ml of chilled water was poured into the reaction mixture to separate the methylene chloride layer. The water layer was further extracted with 50 ml of methylene chloride. The obtained methylene chloride layer was combined with the above methylene chloride layer. The combined layer was washed with water and distilled to remove the solvent. The obtained residue was purified by silica gel column chromatography (with toluene and n-hexane) to obtain 6.6 g of objective 3-chloro-6-ethylthio-2-pyridyl methanesulfonate as a colorless crystal (yield: 93.4%). m.p. 40° to 41° C.

PMR(CDCl$_3$), δ: 1.38 (t, 3H), 3.11 (q, 2H), 3.51 (s, 3H), 7.07 (d, 1H), 7.60 (d, 1H) ppm.

Synthesis Example 7

3,5-Dichloro-6-isobutylthio-2-pyridyl methanesulfonate (No. 82)

6.0 g of 3,5-dichloro-6-isobutylthio-2-pyridinol and 3.0 g of anhydrous sodium carbonate were suspended in 25 ml of N,N-dimethylformamide, followed by stirring. 3.3 g of methanesulfonyl chloride was added dropwise to the suspension at 10° C. The obtained mixture was allowed to stand to lower the temperature to room temperature, heated to 50° C. and stirred for 2.5 hours. The reaction mixture was poured into 200 ml of chilled water and extracted with ether twice. The ether layer was washed with 5% aqueous caustic soda and water, dried over anhydrous sodium sulfate and distilled to remove the solvent. The obtained residue was purified by silica gel column chromatography (with n-hexane and toluene) to obtain 5.8 g of objective 3,5-dichloro-6-isobutylthio-2-pyridyl methanesulfonate as a colorless oil (yield: 73.8%).

$n_D^{25}$ 1.5690

PMR(CDCl$_3$), δ: 1.05 (d, 6H), 1.99 (m, 1H), 3.02 (d, 2H), 3.45 (s, 3H), 7.69 (s, 1H) ppm.

Synthesis Example 8

3,5-Dichloro-6-n-propylsulfinyl-2-pyridyl methanesulfonate (No. 76)

1.5 g of 3,5-dichloro-6-n-propylthio-2-pyridyl methanesulfonate (No. 75) synthesized according to the same procedure as the one described in Synthesis Example 1 was dissolved in 10 ml of acetic acid. 2 ml of 35% aqueous hydrogen peroxide was added dropwise to the obtained solution at 15° C. The obtained mixture was heated to 40° to 50° C., stirred for 5 hours cooled, poured into 200 ml of ice-water and extracted with 50 ml of methylene chloride three times. The methylene chloride layer was washed with 5% aqueous caustic soda three times and with water and an aqueous solution of sodium chloride and dried over anhydrous sodium sulfate.

The oil obtained by distilling away the solvent was purified by silica gel column chromatography (with n-hexane and toluene) to obtain 0.9 g of objective 3,5-dichloro-6-n-propylsulfinyl-2-pyridyl methanesulfonate as a colorless crystal (yield: 43.0%). m.p. 92° to 94° C.

PMR(CDCl$_3$), δ: 1.10 (t, 3H), 1.83 (m, 2H), 3.01 (t, 2H), 3.73 (s, 3H), 7.95 (s, 1H) ppm.

Synthesis Example 9

3,5-Dichloro-6-isobutylsulfonyl-2-pyridyl methanesulfonate (No. 84)

2.38 g of 3,5-dichloro-6-isobutylthio-2-pyridyl methanesulfonate (No. 82) was dissolved in 20 ml of acetic acid. 4 ml of 35% aqueous hydrogen peroxide was added dropwise to the obtained solution at room temperature. The resulting mixture was heated to 80° to 90° C., stirred for 5 hours, cooled, poured into 200 ml of ice-water and extracted with 50 ml of methylene chloride three times. The methylene chloride layer was washed with 5% aqueous caustic soda three times and with water and an aqueous solution of sodium chloride dried over anhydrous sodium sulfate and distilled to remove the solvent, thus obtaining 2.4 g of 3,5-dichloro-6-isobutylsulfonyl-2-pyridyl methanesulfonate as a colorless oil (yield: 91.9%).

$n_D^{25}$ 1.5495

PMR(CDCl$_3$), δ: 1.13 (d, 6H), 2.36 (m, 1H), 3.34 (d, 2H), 3.61 (s, 3H), 8.07 (s, 1H) ppm.

Other compounds of the present invention were synthesized according to the same procedures as the ones described in Synthesis Examples 6 to 9.

Representative compounds among the obtained ones are shown in Table 2.

TABLE 2

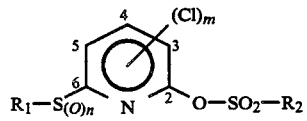

$$R_1-S_{(O)n} \underset{N}{\underset{6}{\overset{5}{\bigcirc}}}\overset{4}{\underset{2}{\overset{3}{(Cl)_m}}} O-SO_2-R_2$$

| No. | R$_1$ | n | R$_2$ | (Cl)$_m$ | Yield (%) | $n_D^{25}$ (mp) | Appearance |
|---|---|---|---|---|---|---|---|
| 70 | CH$_3$CH$_2$— | 0 | CH$_3$ | 3-Cl | 93.4 | (40~41° C.) | colorless crystal |
| 71 | CH$_3$CH$_2$— | 2 | CH$_3$ | 3-Cl | 89.3 | (142~143° C.) | " |
| 72 | (CH$_3$)$_2$CHCH$_2$— | 0 | CH$_3$ | 3-Cl | 92.6 | 1.5540 | pale yellow oil |

TABLE 2-continued $$R_1-S(O)_n \underset{6}{\overset{5}{\bigcirc}}\underset{N}{\overset{4}{\underset{2}{\bigcirc}}}\overset{(Cl)_m}{\underset{3}{\bigcirc}}O-SO_2-R_2$$

| No. | R₁ | n | R₂ | (Cl)ₘ | Yield (%) | n_D²⁵ (mp) | Appearance |
|---|---|---|---|---|---|---|---|
| 73 | (CH₃)₂CHCH₂— | 1 | CH₃ | 3-Cl | 85.8 | (54~55° C.) | colorless crystal |
| 74 | (CH₃)₂CHCH₂— | 2 | CH₃ | 3-Cl | 85.7 | (57~58° C.) | " |
| 75 | CH₃CH₂CH₂— | 0 | CH₃ | 3,5-Cl₂ | 81.5 | (68~69° C.) | pale yellow crystal |
| 76 | CH₃CH₂CH₂— | 1 | CH₃ | 3,5-Cl₂ | 43.0 | (92~94° C.) | colorless crystal |
| 77 | CH₃CH₂CH₂— | 2 | CH₃ | 3,5-Cl₂ | 45.2 | (129~131° C.) | colorless crystal |
| 78 | CH₃CH₂CH₂— | 0 | C₂H₅ | 3,5-Cl₂ | 45.1 | 1.5650 | pale yellow oil |
| 79 | CH₃CH₂— | 0 | CH₃ | 3,5-Cl₂ | 87.7 | (108~109° C.) | pale yellow crystal |
| 80 | CH₃CH₂— | 1 | CH₃ | 3,5-Cl₂ | 83.7 | (92~93° C.) | colorless crystal |
| 81 | CH₃CH₂— | 2 | CH₃ | 3,5-Cl₂ | 81.5 | (130~132° C.) | " |
| 82 | (CH₃)₂CHCH₂— | 0 | CH₃ | 3,5-Cl₂ | 73.8 | 1.5690 | colorless oil |
| 83 | (CH₃)₂CHCH₂— | 1 | CH₃ | 3,5-Cl₂ | 77.6 | (90~91° C.) | colorless crystal |
| 84 | (CH₃)₂CHCH₂— | 2 | CH₃ | 3,5-Cl₂ | 91.9 | 1.5495 | colorless oil |
| 85 | n-C₈H₁₇— | 0 | CH₃ | 3,5-Cl₂ | 82.2 | 1.5472 | pale yellow oil |
| 86 | n-C₈H₁₇— | 1 | CH₃ | 3,5-Cl₂ | 67.6 | 1.5410 | colorless oil |
| 87 | n-C₈H₁₇— | 2 | CH₃ | 3,5-Cl₂ | 92.4 | (70~71° C.) | colorless crystal |
| 88 | CH₃CH₂CH₂CH(CH₃)— | 0 | CH₃ | 3,5-Cl₂ | 90.9 | (38~39° C.) | " |
| 89 | CH₃CH₂CH₂CH(CH₃)— | 1 | CH₃ | 3,5-Cl₂ | 90.8 | 1.5605 | colorless oil |
| 90 | CH₃CH₂CH₂CH(CH₃)— | 2 | CH₃ | 3,5-Cl₂ | 77.8 | 1.5435 | pale yellow oil |
| 91 | (CH₃)₂CH—CH₂— | 0 | ClCH₂CH₂CH₂— | 3,5-Cl₂ | 92.0 | 1.5652 | colorless oil |
| 92 | (CH₃)₂CH—CH₂— | 2 | ClCH₂CH₂CH₂— | 3,5-Cl₂ | 82.1 | (80~81° C.) | colorless crystal |
| 93 | n-C₁₂H₂₅— | 0 | CH₃ | 3,5-Cl₂ | 82.8 | (51~53° C.) | colorless crystal |
| 94 | (CH₃)₂CHCH₂— | 0 | CF₃ | 3,5-Cl₂ | 78.8 | 1.5121 | colorless oil |

FORMULATION EXAMPLE

Formulation Example 1: Emulsifiable concentration 20 parts of a compound of the present invention was dissolved in 65 parts of a xylene/methylnaphthalene mixture. 15 parts of a mixture of an alkylphenol/ethylene oxide condensate and calcium alkylbenzenesulfonate in a ratio of 8:2 was mixed with the obtained solution to prepare an emulsifiable concentration. This emulsifiable concentration may be used as a spreading agent by diluting with water.

Formulation Example 2: Wettable powder 20 parts of a compound of the present invention was mixed with 35 parts of kaolin, 30 parts of clay and 7.5 parts of diatomaceous earth. 7.5 parts of a mixture of sodium laurate and sodium dinaphthylmethanesulfonate in a ratio of 1:1 was added to the obtained mixture. The resulting mixture was finely ground to prepare a powder. This powder may be used as a spreading agent by diluting with water.

Formulation Example 3: Dust 1 part of a compound of the present invention was mixed with 97 parts of a mixture of talc and calcium carbonate in a ratio of 1:1. The resulting mixture was ground to prepare a homogeneously dispersed mixture. 2 parts of silicic anhydride was added to this mixture. The resulting mixture was mixed and ground to prepare a dust. This dust may be used as a spreading agent as such.

Formulation Example 4: Granule 2 parts of a compound of the present invention was mixed with 48 parts of finely powdered bentonite, 48 parts of talc and 2 parts of sodium ligninsulfonate, followed by the addition of water. The resulting mixture was kneaded until it became homogeneous. The mixture was granulated by passing it through an injection molding machine and adjusted to a granular size of 0.6 to 1 mm by passing the granule thus molded through a spherizer and a drying screen classifier. The obtained granule may be directly spreaded on the surface of paddy fields and uplands as such.

Formulation Example 5: Oil

A mixture of 0.1 part of a compound of the present invention and 0.5 part of piperonyl butoxide was dissolved in such an amount of illuminating kerosine as to give the total volume of 100 parts to prepare an oil. This oil may be used as such.

Formulation Example 6: Aerosol 0.4 part of a compound of the present invention, 20 parts of piperonyl butoxide, 6 parts of xylene and 7.6 parts of deodorized kerosene were mixed and dissolved. After filling the mixture into an aerosol container, a valve was fitted. 86 parts of Freon was introduced into the container through the valve under pressure to obtain an aerosol.

Formulation Example 7: Heating fibrous fumigant pesticidal composition 0.05 g of a compound of the present invention was dissolved in an appropriate amount of chloroform. The obtained solution was homogeneously adsorbed on the surface of an asbestos (2.5×1.5 mm, 0.3 mm in thickness) to prepare a fibrous fumigant pesticidal composition of hot plate heating type.

Formulation Example 8: Mosquito-repellant incense 0.5 g of a compound of the present invention was dissolved in 20 ml of methanol, followed by the addition of 99.5 g of an incense carrier comprising tabu powder, pyrethrum marc and wood powder with a ratio of 3:5:1. The obtained mixture was made homogeneous by stirring. After distilling off the methanol, 150 ml of water was added to the residue and the mixture was sufficiently kneaded, molded and dried to obtain a mosquito-repellant incense.

The effects of the present invention will be described by the following Test Examples.

The compounds used in the Test Examples as a control are the following compounds (A), (B) and (C). These compounds were also tested according to the same method as the one for the test of compounds of the present invention.

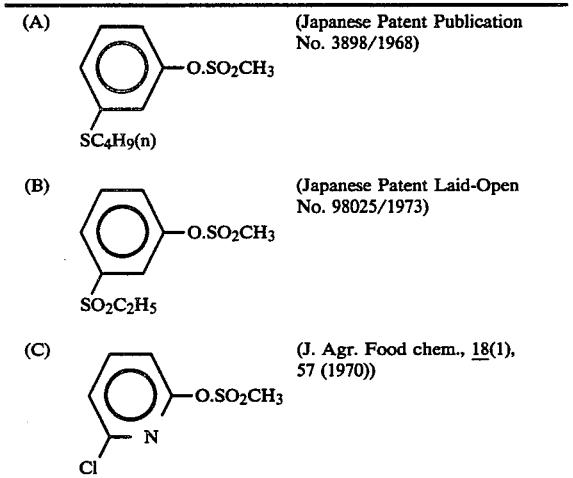

TEST EXAMPLE

Test Example 1: Effect on susceptible strains of Nephotettix cincticeps and resistant strains of Nephotettix cincticeps The compounds of the present invention described in Table 3 were formulated according to the same procedures as the ones described in Formulation Examples 1 and 2 into 20% wettable powders when they were crystal, or into 20% emulsifiable concentration when they were oils, and were used for this test. Further a 50% emulsifiable concentration of BPMC (2-sec-butylphenyl methylcarbamate) and a 40% emulsifiable concentration of diazinon(diethyl 2-isopropyl-4-methyl-6-pyrimidinyl phosphorothionate) were used as a control. Method: 5 to 6 rice plants in the tri- to tetra foliate stages were dipped in 200 ppm chemical solutions for 15 seconds. After air-drying, the plants were placed in a glass cylinder ($\phi$4.5×15 cm). Then, ten female adults of Nephotettix cincticeps, susceptible strain (collected in Ageo city) and ten resistant strain (resistant to both organophosphorus and carbamates collected in Nakagawara, Masaki-cho and in Izumi) were transferred into the cylinder. After covering with a wire mesh, the cylinder was left in a temperature-controlled green house. 48 hours after treatment, the number of dead insects was counted to calculate the mortality. The results shown in Table 3 are averages of two replications.

TABLE 3

| Compound No. | Mortality (%) Susceptible (collected in Ageo) | Resistant (collected in Nakagawara) | Resistant (collected in Izumi) |
|---|---|---|---|
| 1 | 100 | 100 | 100 |
| 2 | 100 | 100 | 100 |
| 3 | 100 | 100 | 100 |
| 4 | 100 | 100 | 90 |
| 5 | 100 | 100 | 70 |
| 6 | 100 | 100 | 80 |
| 7 | 100 | 100 | 100 |
| 8 | 100 | 100 | 100 |
| 9 | 100 | 100 | 100 |
| 10 | 100 | 100 | 100 |
| 11 | 100 | 100 | 100 |
| 12 | 100 | 100 | 100 |
| 13 | 100 | 100 | 100 |
| 20 | 100 | 100 | 90 |
| 21 | 100 | 100 | 100 |
| 22 | 100 | 100 | 100 |
| 23 | 100 | 100 | 100 |
| 24 | 100 | 100 | 100 |
| 26 | 100 | 100 | 100 |
| 27 | 100 | 100 | 100 |
| 28 | 100 | 90 | 80 |
| 29 | 100 | 100 | 100 |
| 30 | 100 | 90 | 90 |
| 31 | 100 | 100 | 70 |
| 32 | 100 | 70 | 100 |
| 33 | 100 | 100 | 100 |
| 34 | 100 | 100 | 100 |
| 37 | 100 | 100 | 100 |
| 42 | 100 | 100 | 100 |
| 43 | 100 | 100 | 90 |
| 50 | 100 | 70 | 60 |
| 59 | 80 | 90 | 80 |
| 64 | 100 | 100 | 100 |
| 65 | 100 | 100 | 100 |
| 66 | 100 | 100 | 100 |
| 67 | 100 | 100 | 100 |
| 68 | 100 | 100 | 100 |
| 69 | 100 | 100 | 100 |
| 70 | 100 | 100 | 100 |
| 72 | 100 | 100 | 100 |
| 73 | 100 | 100 | 100 |
| 74 | 100 | 80 | 60 |
| 75 | 100 | 80 | 50 |
| 78 | 100 | 70 | 50 |
| 79 | 100 | 90 | 60 |
| 82 | 100 | 100 | 50 |
| 88 | 100 | 100 | 100 |
| Control | | | |
| A | 80 | 30 | 10 |
| B | 100 | 20 | 10 |
| C | 60 | 10 | 40 |
| BPMC | 100 | 0 | 0 |
| Diazinone | 100 | 0 | 0 |

Test Example 2: Effect on *Nilaparvata lugens*

The compounds of the present invention and control compounds described in Table 4 were formulated according to the same procedure as the ones described in Formulation Examples 1 and 2 into 20% wettable powders or into 20% emulsifiable concentration and tested. Method: The same procedure as described in the Test Example 1 were repeated, except that 10 female adults of *Nilaparvata lungens* were used. 48 hours after treatment, the number of dead insects was counted to calculate the mortality. The results shown in Table 4 are averages of two replications. *Nilaparvata lugens*, ten susceptible strains (collected in Kaseda city) and ten resistant strains (resistant to both organophosphorus and carbamates collected in Izumi was used in this test.

TABLE 4

| Compound No. | Mortality (%) Susceptible (collected in Kaseda) | Resistant (collected in Izumi) |
|---|---|---|
| 1 | 100 | 100 |
| 3 | 100 | 80 |
| 4 | 100 | 90 |
| 5 | 100 | 70 |
| 6 | 100 | 80 |
| 7 | 100 | 100 |
| 8 | 100 | 100 |
| 9 | 100 | 100 |
| 19 | 100 | 100 |
| 20 | 100 | 60 |
| 21 | 100 | 100 |
| 22 | 100 | 100 |
| 23 | 100 | 100 |
| 24 | 100 | 100 |
| 25 | 100 | 100 |
| 26 | 100 | 100 |
| 27 | 100 | 100 |
| 29 | 100 | 70 |
| 30 | 100 | 90 |
| 31 | 100 | 100 |
| 33 | 100 | 80 |
| 34 | 100 | 100 |
| 35 | 100 | 80 |
| 36 | 100 | 100 |
| 40 | 100 | 100 |
| 42 | 100 | 100 |
| 55 | 100 | 100 |
| 70 | 100 | 100 |
| 72 | 100 | 100 |
| 73 | 100 | 100 |
| 75 | 100 | 100 |
| 79 | 100 | 100 |
| 88 | 100 | 100 |
| Control | | |
| A | 90 | 30 |
| B | 80 | 20 |
| C | 20 | 10 |
| BPMC | 100 | 0 |
| diazinon | 100 | 20 |

Test Example 3: Effects on larvae of *Culex pipiens pallens*

The compounds of the present invention and control compounds described in Table 5 were formulated into 0.1% acetone solutions and tested.

Method: 199.8 ml of well water was placed in a plastic container having a diameter of 9 cm. Twenty larvae of *Culex pipiens pallens* (third to forth instar), collected in Ageo city were transferred into the container. 0.2 ml of the above prepared solution was pipetted into the container to give a chemical solution of 1 ppm. After 24 hours, the number of dead insects was counted to calculate the mortality. The results are shown in Table 5.

TABLE 5

| Compound No. | Mortality (%) | Compound No. | Mortality (%) |
|---|---|---|---|
| 3 | 100 | 12 | 100 |
| 4 | 100 | 13 | 100 |
| 5 | 100 | 14 | 100 |
| 6 | 100 | 15 | 100 |
| 7 | 100 | 19 | 100 |
| 8 | 100 | 20 | 100 |
| 9 | 100 | 21 | 100 |
| 10 | 100 | 22 | 100 |
| 11 | 100 | 23 | 100 |
| | | 24 | 100 |

TABLE 5-continued

| Compound No. | Mortality (%) | Compound No. | Mortality (%) |
|---|---|---|---|
| 25 | 100 | 51 | 100 |
| 26 | 100 | 52 | 100 |
| 27 | 100 | 53 | 100 |
| 28 | 100 | 54 | 100 |
| 29 | 100 | 55 | 100 |
| 30 | 100 | 56 | 100 |
| 32 | 100 | 57 | 100 |
| 33 | 100 | 58 | 100 |
| 34 | 100 | 70 | 100 |
| 35 | 100 | 71 | 100 |
| 36 | 100 | 72 | 100 |
| 37 | 100 | 73 | 100 |
| 38 | 100 | 74 | 100 |
| 39 | 100 | 75 | 100 |
| 40 | 100 | 77 | 100 |
| 41 | 100 | 78 | 100 |
| 42 | 100 | 79 | 100 |
| 43 | 100 | 82 | 100 |
| 44 | 100 | 84 | 100 |
| 45 | 100 | 88 | 100 |
| 46 | 100 | 89 | 100 |
| 47 | 100 | 90 | 100 |
| 48 | 100 | 91 | 100 |
| 49 | 100 | 92 | 100 |
| 50 | 100 | 93 | 100 |
|  |  | 94 | 100 |
| Control |  |  |  |
| A | 80 |  |  |
| B | 20 |  |  |
| C | 0 |  |  |

Test Example 4: Effect on larvae of *Plutella xylostella*

Formulation used: A 20% emulsifiable concentration of the compound of the present invention described in Table 6.

Control: A 40% emulsifiable concentration of MEP (O,O-dimethyl O-4-nitro-m-tolyl phosphorothioate)

Method: A cabbage leaf of a medium size cut from a cabbage grown to decafoliate stage was dipped in a 500 ppm chemical solution for 15 seconds. After air-drying, the leaf was placed in a plastic container (9 cm×6 cm). 15 larvae (third instar) of *Plutella xylostella* were transferred into the container. After covering with a lid having several pinholes, the container was left in a green house at 25° C. 48 hours after the treatment, the number of dead insects was counted to calculate the mortality. The results shown in Table 6 are averages of two replications.

TABLE 6

| Compound No. | Mortality (%) | Compound No. | Mortality (%) |
|---|---|---|---|
| 72 | 100 | 87 | 100 |
| 76 | 100 | 88 | 100 |
|  |  | Control |  |
| 77 | 100 | A | 90 |
| 83 | 100 | B | 60 |
| 84 | 100 | C | 40 |
| 85 | 100 | MEP | 100 |
| 86 | 100 |  |  |

Test Example 5: Effect on larvae of *Chilo suppressalis*

The compounds of the present invention and control compounds described in Table 7 were formulated according to the same procedures as the one described in Formulation Examples 1 and 20 into 20% wettable powders of 20% emulsifiable concentration and tested. Further, a 40% emulsifiable concentration of diazinon (diethyl 2-isopropyl-4-methyl-6-primidinyl phosphorothionate) was used as a control.

Method: 30 to 50 budding unhulled rices were dipped in a 200 ppm chemical solution for 15 seconds. After air-drying, the unhulled rices were placed in a plastic cup having a height of 6.0 cm and a diameter of 9.0 cm. Ten larvae (third instar) of *Chilo suppressalis* were transferred into the container. After covering with a plastic lid, the container was left in a thermohygrostatic room (having a temperature of 25° C.±2° C. and a humidity of 80%±10%). 24 hours after the treatment, the number of dead insects was counted to calculate the mortality. The results shown in Table 7 are average of two replications.

TABLE 7

| Compound No. | Mortality (%) | Compound No. | Mortality |
|---|---|---|---|
| 3 | 100 | 34 | 100 |
| 4 | 100 | 37 | 100 |
| 5 | 100 | 38 | 100 |
| 6 | 100 | 43 | 100 |
| 7 | 100 | 50 | 100 |
|  |  | Control |  |
| 8 | 100 | A | 10 |
| 9 | 100 | B | 0 |
| 10 | 100 | C | 0 |

Test Example 6: Effect on adults of *Tetranychus urticae*

The compounds of the present invention and control compounds described in Table 8 were formulated according to the same procedures as the ones described in Formulation Examples 1 and 2 into 20% wettable powders or 20% emulsifiable concentration and tested.

Method: The primary leaf of a potted kidney bean was trimmed to a size of approximately 3 cm×3 cm. 15 female adults mites susceptible to organophosphorus insecticides were transferred onto the leaf using a small brush. The plant was left in a temperature-controlled room at 25° C. After one day, dead or abnormal mites were taken out of the leaf. The mites on the leaf were dipped in a 400 ppm chemical solution for 10 seconds. After the treatment, the plant was left in the room again. 48 hours after the treatment, the number of dead mites was counted under a stereomicroscope to calculate the mortality. The results are shown in Table 8.

TABLE 8

| Compound No. | Mortality (%) | Compound No. | Mortality (%) |
|---|---|---|---|
| 4 | 100 | 37 | 100 |
| 7 | 100 | 38 | 100 |
| 14 | 100 | 75 | 100 |
| 15 | 100 | 80 | 100 |
| 16 | 100 | 81 | 100 |
| 17 | 100 | 85 | 100 |
| 26 | 100 | 86 | 100 |
|  |  | Control |  |
| 29 | 100 | A | 30 |
| 30 | 80 | B | 50 |
| 31 | 90 | C | 10 |
| 32 | 80 |  |  |

Test Example 7: Effect on the clubroot of tomatoes due to *Meloidogyne incognita*

400 g of soil polluted with *Meloidogyne incognita* was packed in a plastic cup having a diameter of 10 cm. The compounds of the present invention, control compounds of DCIP[bis(2-chloromethylethyl)ether]were formulated according to the same procedure as the one described in Formulation Example 3 into 1% dusts. 40 mg of each dust was applied to the soil, followed by entire mixing. Fifteen seeds (kind: *Ponte rosa*) were sown per cup. 40 days after the chemical treatment, the tomatoes were digged up and examined for damage due to chemicals and clubroot index. The results are shown in Table 9. The clubroot index was calculated by the following expression:

Clubroot index =

$$\frac{(A \times 4) + (B \times 3) + (C \times 2) + (D \times 1)}{\text{number of examined seedlings}} \times 100$$

A: Number of tomato seedlings having at least 31 lumps at the root
B: Number of tomato seedlings having 21 to 30 lumps at the root
C: Number of tomato seedlings having 11 to 20 lumps at the root
D: Number of tomato seedlings having 1 to 10 lumps at the root.

TABLE 9

| Compound No. | Clubroot index | Damage |
|---|---|---|
| 1 | 42 | none |
| 3 | 44 | " |
| 4 | 24 | " |
| 6 | 35 | " |
| 7 | 49 | " |
| 9 | 27 | " |
| 10 | 37 | " |
| 12 | 31 | " |
| 73 | 57 | " |
| 79 | 60 | none |
| 88 | 52 | " |
| Control (C) | 74 | " |
| DCIP | 83 | " |
| not treated | 100 | " |

Test Example 8: Effect on *Thrips palmi*

A 20% emulsifiable concentration of the compounds of the present invention described in Table 10 was prepared according to the same procedure as the one described in Formulation Example 1. A 50% emulsifiable concentration of BPMC (2-sec-butylphenyl methylcarbamate) and a 40% emulsifiable concentration of methiadathion (S-2,3-dihydro-5-methoxy-2-oxo-1,3,4-thiadiazol-3-ylmethyl O,O-dimethyl phosphorodithioate) were used as a control.

Method: Each emulsifiable concentration was diluted with a spreader (New Gramine) which had been diluted 2000 times to prepare a chemical solution having a given concentration. A cucumber leaf was dipped in the chemical solution for 10 seconds, air-dried and placed in a plastic cup having a diameter of 9 cm and a height of 5 cm. Ten larvae of *Thrips palmi* were transferred into the cup. After covering with a lid, the cup was left in a temperature-controlled room at 25° C. After 48 hours, the number of dead insects was counted to calculate the mortality. A 50% lethal concentration (LC$_{50}$ value) was determined from the mortality by the probit method. The results are shown in Table 10.

TABLE 10

| Compound No. | LC$_{50}$ (ppm) |
|---|---|
| 4 | 15 |

TABLE 10-continued

| Compound No. | LC$_{50}$ (ppm) |
|---|---|
| 8 | 7.8 |
| 10 | 20 |
| Control BPMC | >100 |
| methidathion | 43 |

What we claim is:

1. A compound of the general formula:

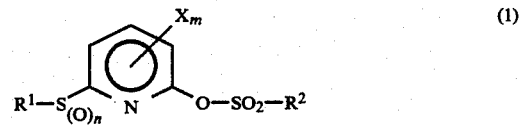

wherein $R^1$ is $C_1-C_{12}$ alkyl, $R^2$ is $C_1-C_{12}$alkyl or $C_1-C_4$ alkyl which is substituted with halogen, X is halogen, m is 0, 1 or 2 and n is 0, 1 or 2.

2. A compound according to claim 1, wherein $R^1$ is $C_1-C_5$alkyl, $R^2$ is $C_1-C_3$alkyl or chloromethyl, X is chloro, m is 0, 1 or 2 and n is 0, 1 or 2.

3. A compound according to claim 2, wherein $R^1$ is $C_2-C_5$ alkyl, $R^2$ is methyl, ethyl or chloromethyl, X is chloro, m is 0 or 1 and n is 0, 1 or 2.

4. A compound according to claim 3, which is selected from the group consisting of

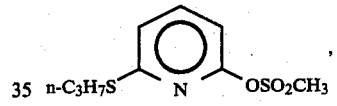

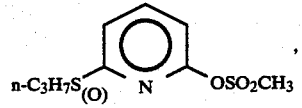

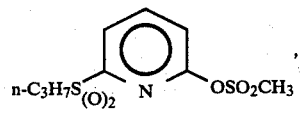

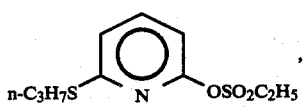

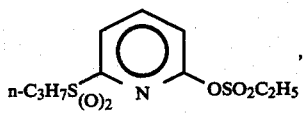

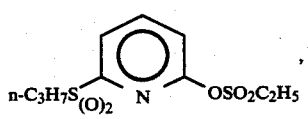

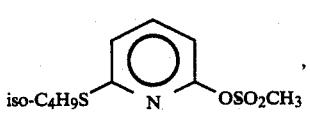

-continued

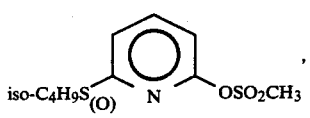,

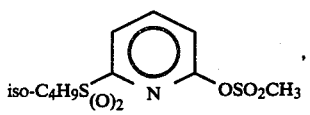,

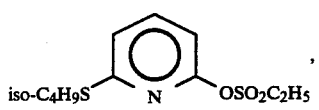,

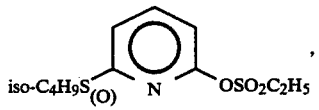,

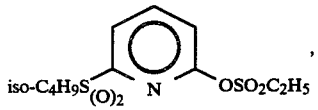,

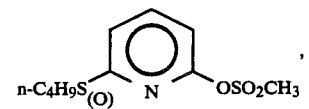,

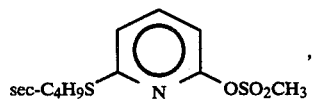,

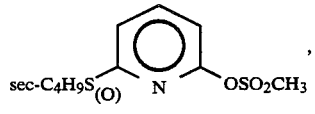,

-continued

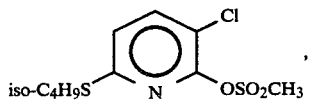,

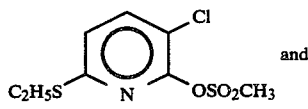 and

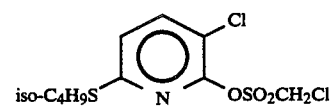

5. An insecticidal, acaricidal or nematicidal composition comprising an effective amount of a compound of the formula:

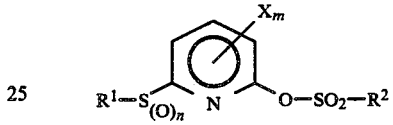

wherein $R^1$ is $C_1$-$C_{12}$alkyl, $R^2$ is $C_1$-$C_{12}$ alkyl or $C_1$-$C_4$ alkyl which is substituted with halogen, X is halogen, m is 0, 1 or 2 and n is 0, 1 or 2, as an effective component in combination with an inert carrier.

6. A method for killing insect pests, acarids or nematodes, which comprises applying an effective amount of a compound of the formula:

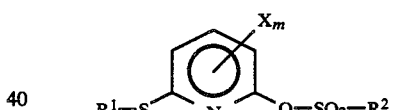

wherein $R^1$ is $C_1$-$C_{12}$alkyl, $R^2$ is $C_1$-$C_{12}$alkyl or $C_1$-$C_4$alkyl which is substituted with halogen, X is halogen, m is 0, 1 or 2 and n is 0, 1, or 2, to said insect pests, acarids or nematodes.

* * * * *